United States Patent [19]

O'Donnell et al.

[11] Patent Number: 5,186,177

[45] Date of Patent: Feb. 16, 1993

[54] METHOD AND APPARATUS FOR APPLYING SYNTHETIC APERTURE FOCUSING TECHNIQUES TO A CATHETER BASED SYSTEM FOR HIGH FREQUENCY ULTRASOUND IMAGING OF SMALL VESSELS

[75] Inventors: Matthew O'Donnell, Ann Arbor, Mich.; Lewis J. Thomas, III, Schenectady, N.Y.

[73] Assignee: General Electric Company, Schenectady, N.Y.

[21] Appl. No.: 803,242

[22] Filed: Dec. 5, 1991

[51] Int. Cl.⁵ .............................................. A61B 8/12
[52] U.S. Cl. ............................ 128/662.06; 128/661.01
[58] Field of Search ..................... 128/660.03, 661.01, 128/660.09, 662.06, 4; 73/625–626

[56] References Cited

U.S. PATENT DOCUMENTS

| 4,841,977 | 6/1989 | Griffith et al. | 128/660.03 |
| 4,911,170 | 3/1990 | Thomas et al. | 128/660.03 X |
| 4,917,097 | 4/1990 | Proudian et al. | 128/662.06 |
| 5,027,659 | 7/1991 | Bele et al. | 128/661.01 X |

Primary Examiner—Francis Jaworski
Attorney, Agent, or Firm—Marvin Snyder

[57] ABSTRACT

A catheter based ultrasound imaging system is disclosed which is capable of providing images of coronary vessels at frequencies near 50 MHz. The catheter based system implements a Synthetic Aperture Focusing Technique (SAFT) by scanning through a miniature ultrasound transducer array to sequentially select and fully multiplex a subset of array elements to operate as a sub-aperture of the total synthetic aperture on each firing; thus reducing the number of required catheter interconnections. Each synthetic aperture array is dynamically and retrospectively focused to accommodate precision imaging at high frequency without conventional signal to noise losses.

14 Claims, 10 Drawing Sheets

METHOD AND APPARATUS FOR APPLYING SYNTHETIC APERTURE FOCUSING TECHNIQUES TO A CATHETER BASED SYSTEM FOR HIGH FREQUENCY ULTRASOUND IMAGING OF SMALL VESSELS

CROSS-REFERENCE TO RELATED APPLICATIONS

The invention disclosed and claimed herein is related to the subject matter of the following commonly assigned patent applications, the entire disclosures of which are hereby expressly incorporated herein by reference:

Commonly assigned copending patent application Ser. No. 07/451,060 entitled IMAGING APPARATUS AND METHOD WITH REDUCED NUMBER OF INTERCONNECTING WIRES by Lewis J. Thomas et al filed Dec. 15, 1989, and now abandoned, disclosing and claiming a catheter based apparatus which reduces the required number of interconnecting wires by multiplexing only received signals from a transceiver array operating in echo mode;

Commonly assigned copending patent application Ser. No. 07/767,460 entitled DYNAMIC TRANSMIT FOCUSING OF A STEERED ULTRASONIC BEAM, by Matthew O'Donnell filed Sep. 30, 1991, disclosing and claiming a phased array sector scanning system for correcting only received ultrasonic signals to dynamically focus the total transmit/receive beam.

1. Field of Invention

The present invention relates generally to a method and apparatus for acquiring data using a Synthetic Aperture Focusing Technique (SAFT) applied to a catheter based imaging system and more specifically to a system for simultaneously multiplexing signals transmitted and received by sampling a miniature ultrasound transducer array wherein the sampled subarray is designed to operate as an iterative subset of a dynamically focused synthetic aperture array accommodating a reduced number of required electrical interconnections without unacceptable loss in signal to noise ratio.

2. Background of the Invention

Current interest in intravascular ultrasound imaging using catheter based diagnostics is driven by an increasing need to manage the development of atherosclerotic disease particularly in the coronary arteries. A basic catheter tip capable of being inserted into vessels down to the size of a coronary artery requires restricting outer diameter dimensions to about 1.2 mm. The inner diameter of the catheter must be maintained at about 1 mm to accommodate manipulation of auxiliary interventional hardware. This leaves only about a 100 μm annulus for housing an operational ultrasound transducer array with active electronics and necessary external interconnection cables. Recent work by G. R. Lockwood, et al entitled "High frequency vascular tissue characterization", Proceedings of the 1990 IEEE Ultrasonics Symposium 90CH2938-9 pp. 1409-12 (1990) suggests the possibility of imaging in the 50-100 MHz range in small vessels. At 50 MHz, the wavelength (λ) of ultrasound is about 30 μm in soft tissue. Typical ultrasound systems either cannot practically accommodate the necessary 1.6λ-3.3λ resolution at this high frequency or can only provide requisite resolution over a limited range. Array systems have been developed and integrated into a catheter tip. However, the basic tradeoff for a conventional catheter array system addresses the inverse relationship between the number of necessary external interconnections (cables) and the degree of beam forming control. The size of an aperture synthesized from individual array elements is limited by the angular response (or directivity) of the individual array elements. Few cables generally imply large elements; and large elements generally have a limited acceptance angle resulting in poor beam forming capability. Thus, in order to limit the number of cables and still provide a sufficiently large synthetic aperture, the aperture can be electronically synthesized from a plurality of array elements. However, the plurality of array elements are typically large resulting in poor beam forming capacity. Conventionally, a wide aperture lens with good beam forming characteristics and adequate signal to noise ratio over a substantial range can be synthesized using conventional phased array principles but generally only with a large number of cable connections. Thus, a conventional phased array approach does not accommodate the interconnecting wire limitations inherent in providing a high frequency catheter capable of insertion into small coronary vessels for high frequency diagnostic imaging thereof. Although a single element synthetic aperture system produces a high resolution beam profile, the impedance of an individual element can be unacceptably high. Consequently, individual array element impedance combined with the low acoustic power delivered to each element have made conventional, sequential, one at a time firing of multiple individual elements comprising an array a generally unacceptable approach to high frequency synthetic aperture imaging in coronary vessel catheter applications.

The entire process of synthetic aperture reconstruction can simply be reduced to a complex filtering operation on a plurality of individual array element signals according to commonly assigned copending application Ser. No. 07/767,460.

SUMMARY

In accordance with the instant invention, by stepping through a plurality of signals acquired over a plurality of transducer elements collectively operating as a synthetic aperture, an arbitrary focus can be dynamically achieved by retrospectively time delaying echo signals resulting from each excitation, weighting each individual signal magnitude and phase accordingly, then summing over the plurality, said plurality being configured to accommodate both acceptable beam directivity and adequate signal to noise criterion.

To accomplish this, a multiplexor is disposed within a catheter small enough to be disposed within a coronary artery, the multiplexor being controlled by a single cable. The multiplexor provides connection, in a parallel manner, to a plurality of contiguous transceiver array elements operating as a fully multiplexed dynamically focused subarray of a synthetic aperture. This subarray comprises a subset of miniature transducer elements operating as a synthetic aperture wholly disposed about the catheter in a manner suitable for performing coronary vessel imaging preferably in the range of 50 MHz. Each transceiver element is multiplexed on both transmit and receive providing a beam that is focused in pulse-echo mode. The multiplexor preferentially scans throughout the entire miniature transducer array by incrementally connecting a select plurality of transducer elements to operate as a transceiver subarray for each excitation pulse wherein selection generally proceeds by consecutively incrementing and decrementing at least one element from the multiplexor. Each select plurality of multiplexor connected elements operates as a subarray or subaperture of the total synthetic aperture, being simultaneously pulsed in a parallel manner on transmit for each excitation pulse. Scanning sequentially proceeds in this manner to electronically sample throughout the entire miniature transducer array. The number of transducer array elements comprising the sub-aperture for each excitation pulse is selected to provide sufficient beam directivity as well as acceptable impedance matching. Complex filtering is employed to dynamically focus a pulse-echo beam using signals obtained from the entire synthetic aperture over a collection of excitation pulses.

In the preferred embodiment of the invention, the entire array of transducers is preferentially disposed circumferentially about a sufficiently small tubular catheter, cross-sectionally comprising a circular transducer array. The plurality of array elements comprising the subaperture is then selected by sequentially decrementing one element of the circular array from the multiplexor and incrementing the next sequential element to the multiplexor; thus, incrementally stepping through the circular array operationally forming a rotating subarray which remains stationary on each firing. In this way, the synthetic aperture subarray is operationally analogous to a classic linear array rotating about the circular transducer array, as this incremental stepping process proceeds about the circular array preserving the same operative sub-aperture size on each firing. Furthermore, elements are spaced so as to provide a spatial sampling frequency consistent with the Nyquist condition in order to avoid artifacts due to insufficient sampling.

OBJECTS OF THE INVENTION

It is recognized that imaging methodology must be developed that minimizes the number of cables exiting a catheter, permits easy image reconstruction using conventional electronics, and results in an affordable catheter.

It is therefore an object of this invention to provide an inexpensive high frequency (preferably 50 MHz) ultrasound data acquisition system and associated electronics capable of being housed in a catheter small enough to be easily disposed in a small coronary vessel for imaging thereof.

It is another object of the invention to provide a minimum number of required cables to such a catheter.

Still another object of the invention is to utilize Synthetic Aperture Focusing Techniques (SAFT) wherein each transceiver element of a suitably designed array is multiplexed on transmit and receive.

A further object of the invention is to improve impedance matching to preserve the integrity of imaging signals obtained from multiple elements comprising a subaperture of the total synthetic aperture.

Yet another object of the invention is to dynamically focus the pulse-echo beam using a complex filtering process.

BRIEF DESCRIPTION OF THE DRAWINGS

While the novel features of the invention are set forth with particularity in the appended claims, the invention, both as to organization and content, will be better understood and appreciated, along with other objects and features thereof, from the following detailed description taken in conjunction with the drawings in which:

DETAILED DESCRIPTION OF THE INVENTION

Figure 1A:
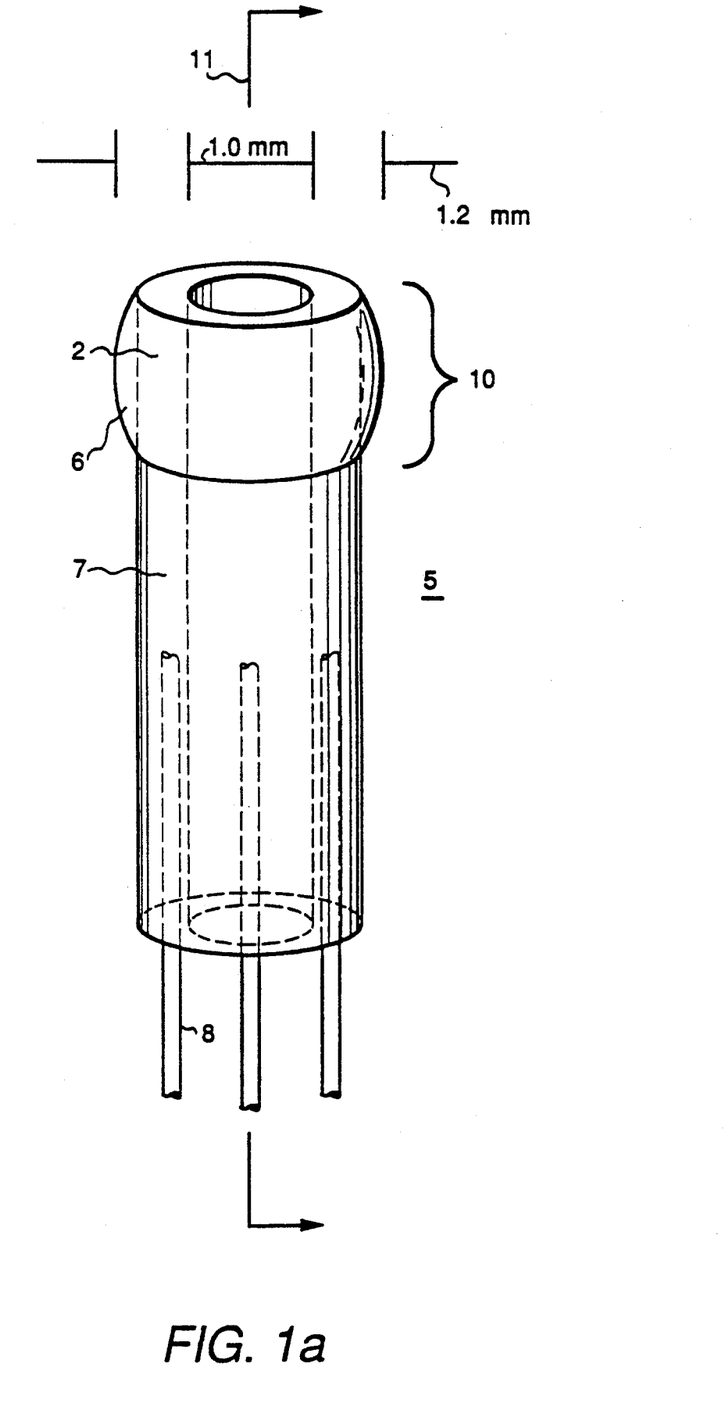
FIGS. 1a, 1b and 1c illustrate perspective, plan, and cross sectional views respectively of an ultrasound catheter small enough for imaging a small coronary vessel and requiring at most three operational cables beyond routine power and ground cables.
Figure 1B:
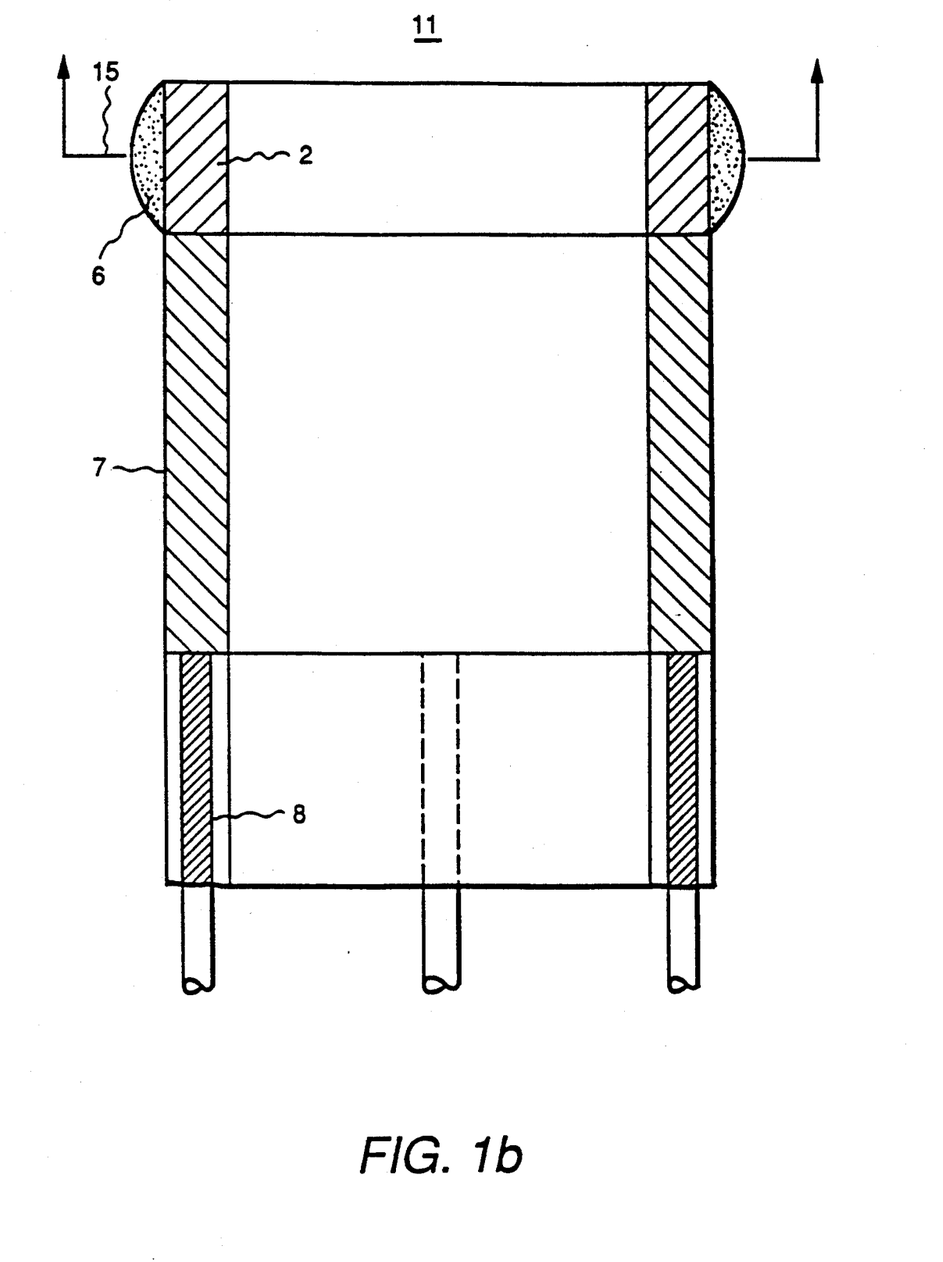
Figure 1C:
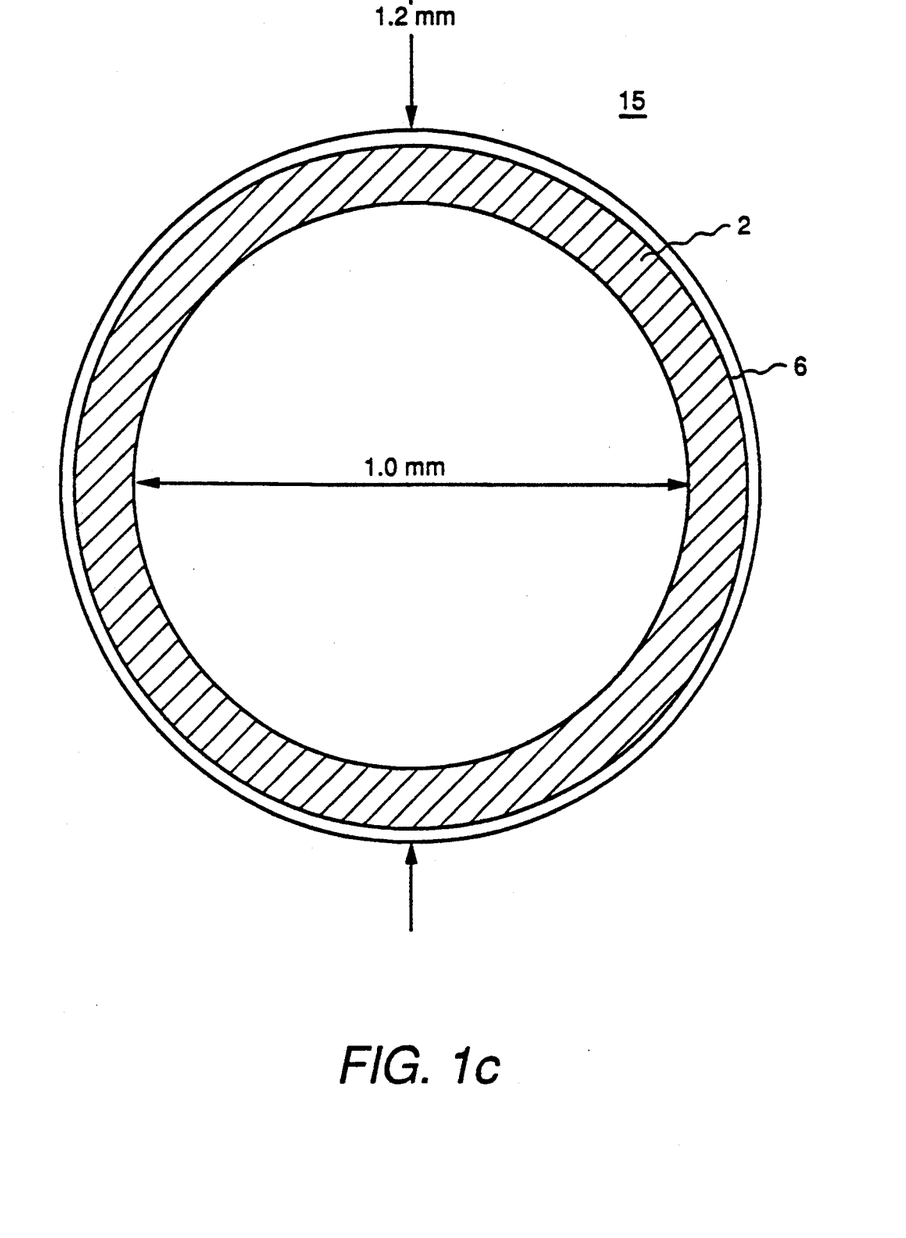

FIG. 1a illustrates a perspective view of a basic catheter 5 designed for insertion into vessels as small as a coronary artery. Ultrasound catheter 5 consists of a transducer array (not shown) housed in catheter tip 10 which in part operates as a transceiver subarray capable of transmitting and receiving through the same transducer array subset; an acoustic lens feature 6; tubular housing 7 for electronics (not shown) necessary to accommodate active operation of the transceiver subarray; and at most three necessary cables, one of which is indicated at 8. These include three operational cables required to transmit, receive and control signals for imaging; as well as a power cable (not shown) and an electrical ground cable (not shown). Alternatively, control signals can be passed over a single transmit/receive signal cable so that only one operational cable need pass from the console to the catheter tip. FIG. 1b presents a plan view, taken in the direction indicated by numeral 11 of FIG. 1a, to illustrate the area accommodated by interventional hardware such as a balloon angioplasty device or the like. This area is presented in contrast to the relatively small space 7 available for active catheter electronics and the equally small annular space 2 available for disposition of the ultrasound transducer array. To accommodate the dimensional constraints imposed for insertion into vessels the size of coronary arteries, catheter tip 10 must not exceed stringent geometrical constraints. In order to appreciate these dimensional constraints, FIG. 1c presents a cross sectional view taken through plane 15 as indicated in FIG. 2b. Tubular catheter tip 10 has an outer diameter no larger than 1.2 mm. The inner diameter of catheter tip 10 must be maintained at about 1.0 mm to allow easy manipulation of various types of interventional hardware. Therefore, the entire ultrasound transducer array is housed within a 100 μm tubular annulus indicated at numeral 2. In order to fully accommodate the physical proximity constraints of catheter tip 10 for high frequency pulsing, preferably at about 50 MHz, a miniature transducer array and associated high frequency electrical interconnections are integrally constructed using typical photolithographic fabrication processing and disposed about a suitable support structure for disposition within catheter tip 10.

Figure 2:
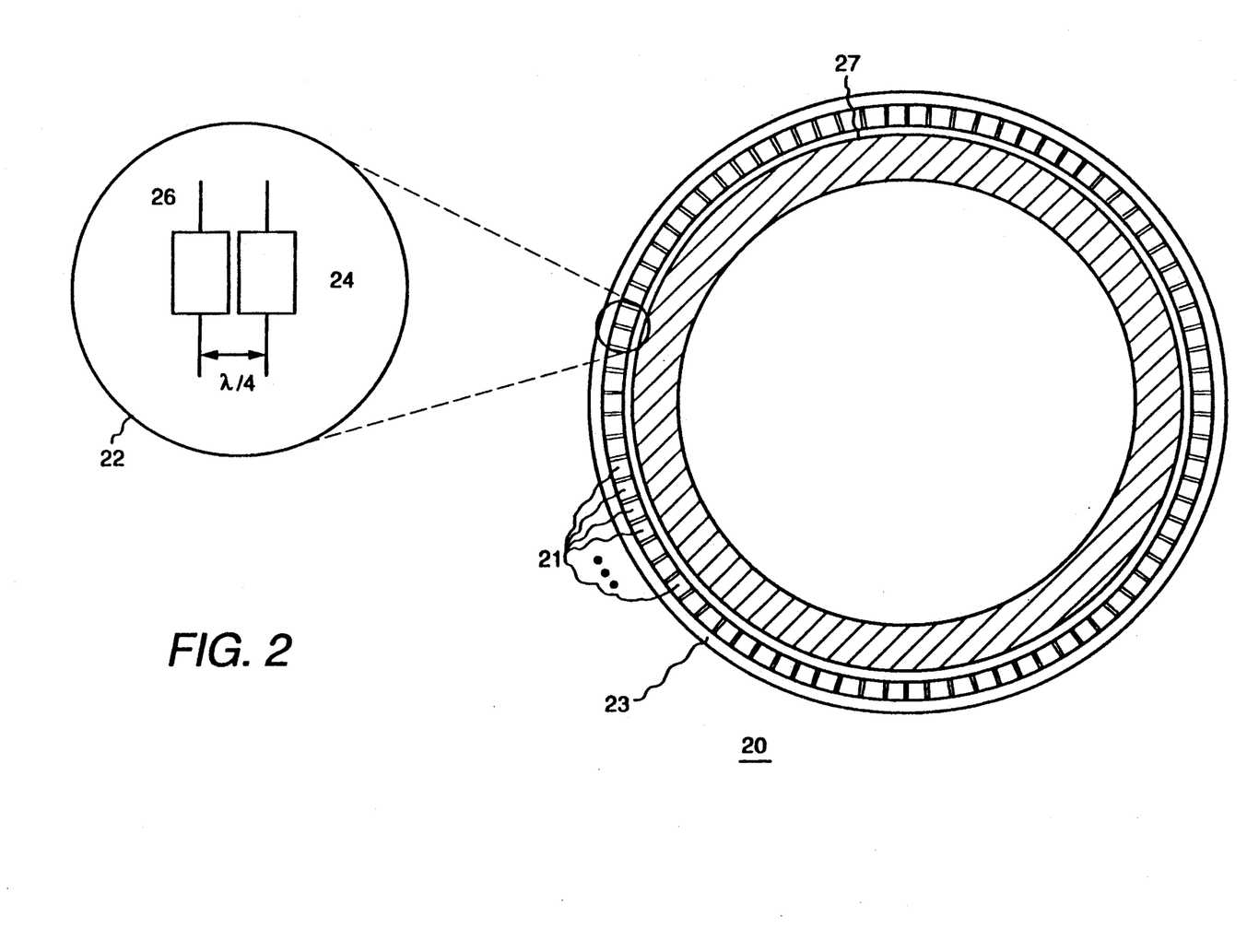
FIG. 2 illustrates a multi-element transducer array disposed within the catheter tip of FIG. 1c having elements spaced apart so as to accommodate Nyquist sampling.

FIG. 2 illustrates such an integrally fabricated miniature transducer array 20 having a plurality of elements 21 disposed circumferentially about a suitable tubular support structure 27, the entirety of which is disposed within annulus 2 (as indicated in FIGS. 1a-1c). Transducer array elements have equal, $\lambda/4$, spacing as shown in an enlarged exploded view identified by numeral 22. Requiring $\lambda/4$ spacing assures spatial sampling frequency will satisfy the Nyquist theorem in order to avoid sampling artifacts, e.g. grating lobes, which may develop during image reconstruction due to insufficient sampling. The plurality of miniature transducer elements, one of which is shown in exploded view at numeral 24, and the corresponding plurality of miniature transmission lines, one of which is shown in exploded view at numeral 26, are fabricated using a conventional photolithographic technique. Photolithographic fabrication processing (not shown) is carried out on a rigidly flat support structure; however the resultant film bound array 20 is flexible when removed from the processing support structure and can be wound around the outer surface of tubular support structure 27 for disposition in catheter tip 10 (see FIGS. 1a-1c). A thin film 23 of silicone rubber (about 10 $\mu$m thick) is deposited over array 20 protecting transducer elements and corresponding electrical interconnections, e.g. 24 and 26, as well as providing an acoustic lens feature (see 6 of FIGS. 1a-1c) in the plane orthogonal to the scan plane of the imaging system. Miniature electrical transmission lines e.g. 26 connect each array element e.g. 24 to an n:m multiplexor, where n is the total number of elements in array 20, and m is the number of available multiplexor channels.

Figure 3:
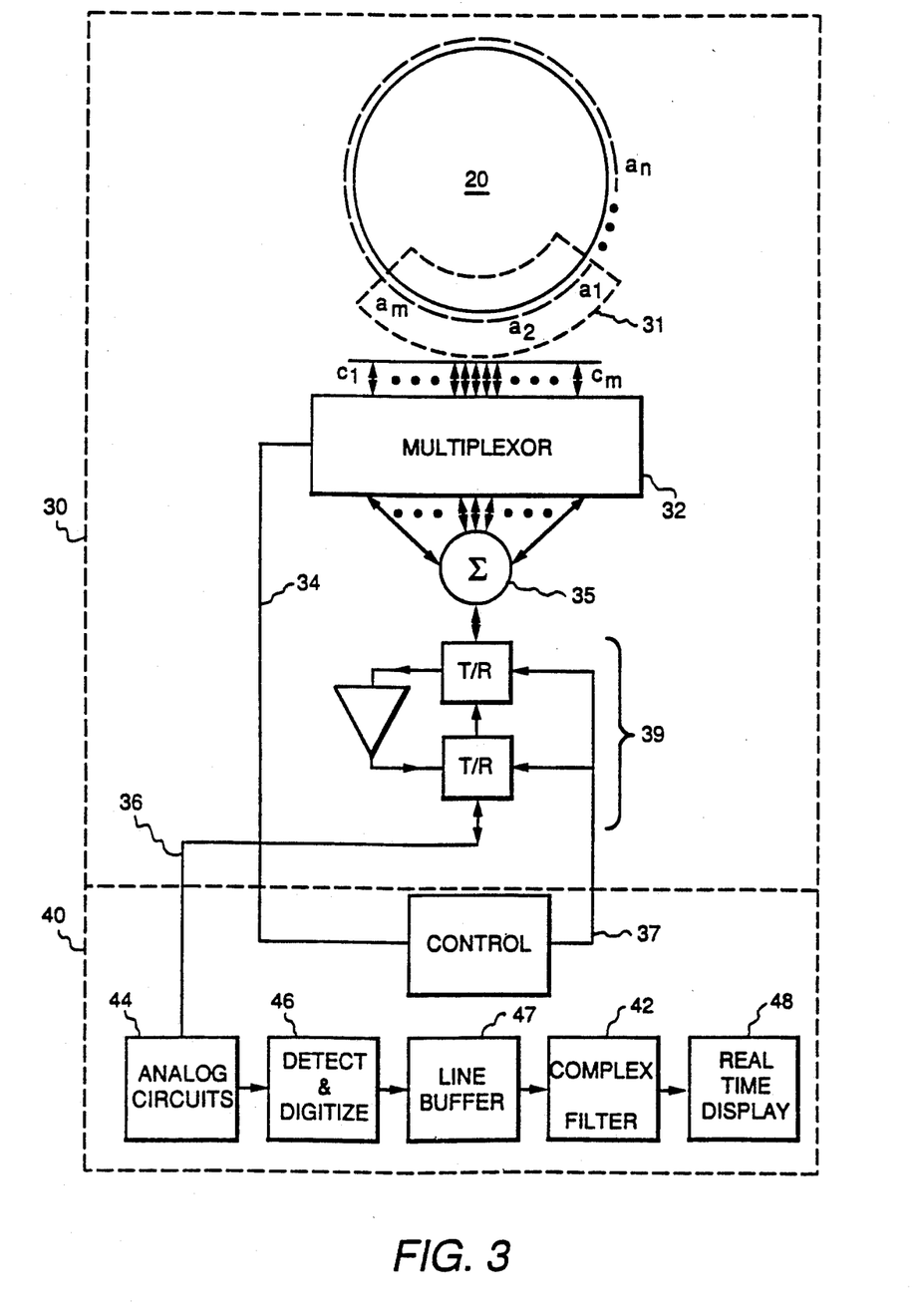
FIG. 3 illustrates a catheter based imaging system having a fully multiplexed transceiver subarray wherein an optimal filtering approach is employed using SAFT reconstruction to provide a dynamically focused image of a small coronary vessel in accordance with the invention.

FIG. 3 illustrates, in accordance with the invention, multiplexing of m of the n elements of circular transducer array 20 as described in FIG. 2, being disposed within catheter tip 10 as described in FIGS. 1a-1c. Circular transducer array 20 is comprised of a plurality of n elements ($a_1, a_2, \ldots a_n$). Multiplexor 32 is controlled by a single cable 34, wherein at any firing, m contiguous elements ($a_1, a_2, \ldots a_m$) are connected in parallel to m corresponding multiplexor channels ($c_1, c_2, \ldots c_m$) in order to form an m element long subarray as identified at 31. For each firing of transducer array 20, only m elements are utilized for both transmission and reception i.e. transducer elements (1-m) operate as transceiver elements (1-m). However, from one firing to the next, the transceiver center point is spatially incremented by one element. For example, if m=16, then on firing number 1 elements 1-16 are coupled through the 16 channel multiplexor to operate as subarray 31; whereas on firing number 2 elements 2-17 are coupled through the 16 channel multiplexor to operate as subarray 31. Incremental scanning proceeds in this stepwise fashion, sequentially rotating about the entire circular array 20 of transducers preserving the same number of subarray transducers.

In accordance with the invention, utilizing the data acquisition method just described so simplifies probe construction as to make possible a system that meets the proximity and cabling constraints of FIGS. 1a-1c. By using such a configuration, only a single RF stage is required to simultaneously pulse the m elements operating as subarray 31. As long as m is a relatively large number, the effective capacitance that RF channel 36 experiences does not distort receive signals for imaging. This is a significant improvement as a large number of elements comprising an array typically have little individual capacitance, each element's capacitance typically being less than 1 pf. In accordance with the invention, at most three cables (aside from power and ground which are not shown) are needed to communicate with the catheter: an RF channel 34, a multiplexor control channel 36, and a transmit/receive (T/R) switch control channel 37. Since control information is passed to the catheter tip during time intervals not used for imaging, control information can alternatively be passed over RF cable 36 alone, resulting in only a single requisite cable for communication with the catheter. Transducer array 20, multiplexor 32, summing circuit 35 and transmit/receive switching circuitry 39 are all housed within catheter 5, as described in FIGS. 1a-1c and 2, being indicated by dotted enclosure 30 in FIG. 3. All other imaging electronics are disposed external to catheter 5 as indicated by dotted enclosure 40. Multiplexor 32 is specially designed to be disposed within catheter tip 10, yet capable of handling high voltages (>100 V) and high bandwidths (>75 MHz) with very little parasitic capacitance. In the preferred embodiment multiplexor 32 utilizes a GaAs FET array.

Figure 4:
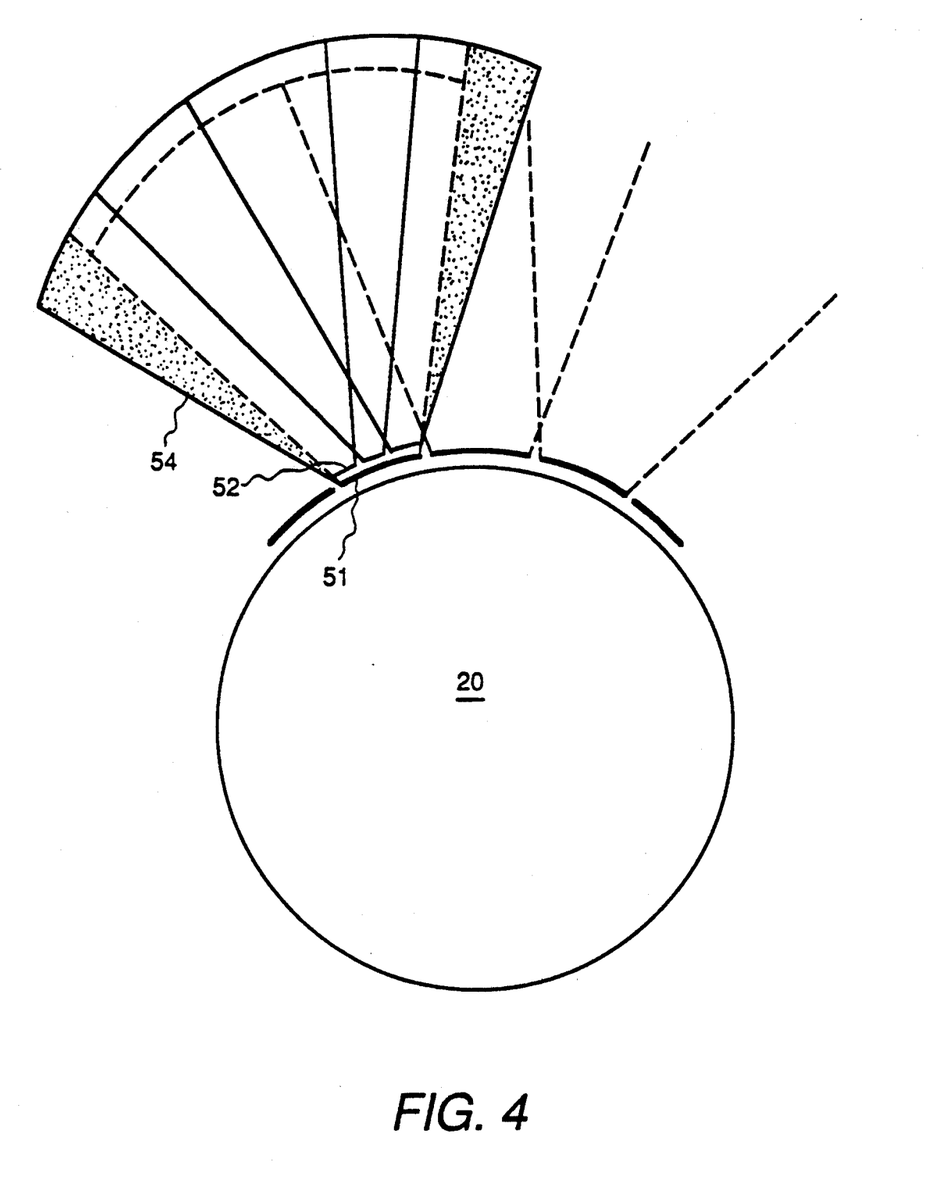
FIG. 4 illustrates the impact of diffraction limited resolution on multi-element synthetic aperture design.

In accordance with the invention, an effective subarray 31 is designed to tie together enough simultaneously pulsed multiple array elements to effectively increase signal to noise ratio; but few enough to maintain adequate beam directivity. To make this point, the effect of subarray 31 design on beam directivity is illustrated in FIG. 4 for a circular transducer array 20 wherein the effect of the size of the subarray elements on beam directivity is indicated. Angular response from each uniform, equally spaced large array element e.g. 51 is shown in dotted lines. There must be significant overlap between adjacent elements to permit characterization of the plurality as an independent subarray of a full synthetic aperture. The size of a synthesized subarray (i.e. the value of m) is diffraction limited by the angular response of each individual array element for the frequency of interest, herein preferably 50 MHz. The use of smaller multiple individual elements e.g. 52 to form a subarray spatially equivalent to single element 51 operates to narrow the beam by an angular spread shown dotted at 54 in FIG. 4; thus, contributing to diffraction limited resolution. Therefore, a large number of elements in the subarray enhances impedance matching to electronics; while narrowing the resultant beam; these effects together operate to limit the overall capability to form a large synthetic aperture. To accommodate these competing effects, an optimal choice of subarray size is provided which balances impedance matching and resultant beam directivity.

Returning to FIG. 3, reconstruction is performed in accordance with an imaging system utilizing complex filtering as disclosed in commonly assigned copending patent application Ser. No. 07/767,460. Reconstruction means of the type shown in FIG. 3 at 40 perform such complex filtered image processing. Correction is made to the receive beam to offset errors caused by the transmit beam being out of focus at all but its fixed focal range. Complex aperture correction coefficients are calculated in an off-line manner for each transducer array element and transmit focal distance then stored for recall during the reconstruction procedure. A complex filter function is generated and applied to received signals as indicated at 42 wherein the complex filter function is dependent solely upon range to dynamically focus the pulse-echo synthetic aperture array. The filter coefficients change with range since both the magnitude weighting component and the complex phase weighting component from each element must vary to insure true dynamic focusing. The filtering correction coefficients are so altered to derive optimal filter functions for each multiple element subarray; thus, providing image quality comparable to that of a single element synthetic aperture. In the case of circular array 20 described in FIGS. 2 and 3, independent beams are formed by each of the m elements of synthetic aperture array 31. By requiring these elements to be spaced λ/4 apart it is assured that an undistorted filter function, or complex weighting function, can be independently derived for reconstruction at each range. The hardware identified at numeral 40 of FIG. 3 operates first to digitize a signal using a high frequency analog to digital (A/D) converter 44 operating at a clock frequency equal to four times the carrier frequency of the excitation pulse. This signal is then baseband demodulated using a simple digital baseband circuit 46 to produce a complex output waveform at a sampling rate equal to the carrier frequency. The demodulated signal is then stored in beam buffer 47 for real time display, wherein the buffer is large enough to store one frame's worth of data. The signal components are then processed by complex filter 42 wherein complex filter weighting coefficients (magnitude and phase) are altered as a function of range. Filtered resultant signals are then buffered and scan converted for real time display at 48.

Figure 5:
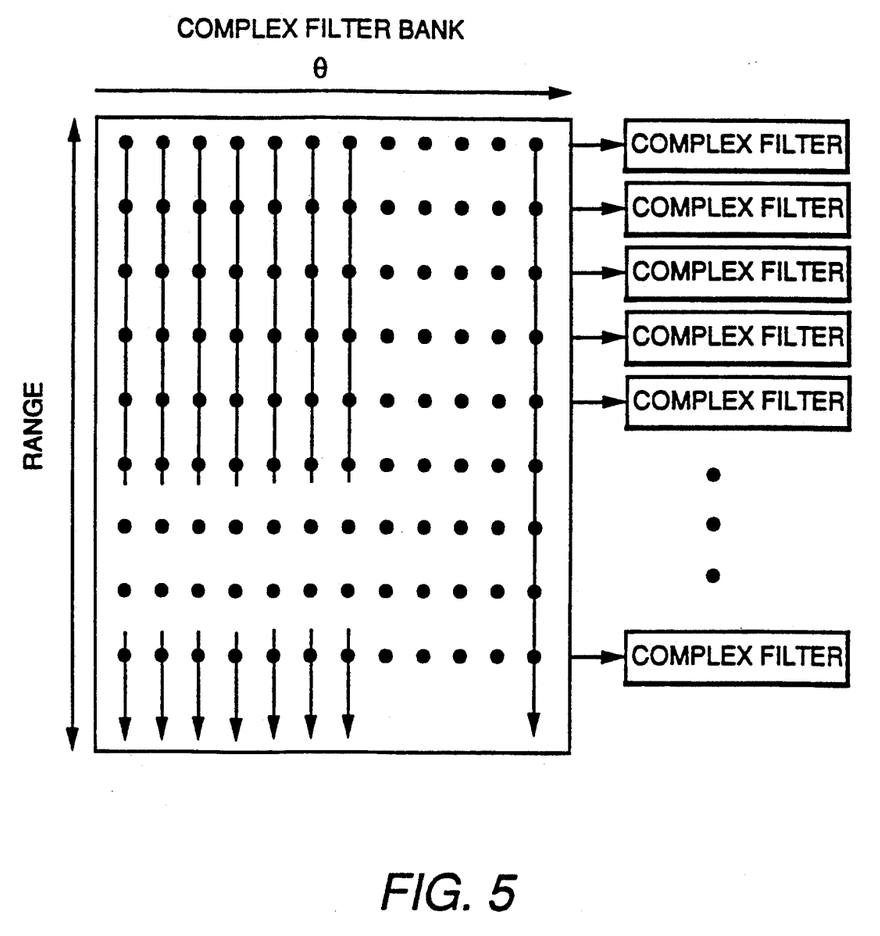
FIG. 5 illustrates a typical complex filter bank.
Figure 6A:
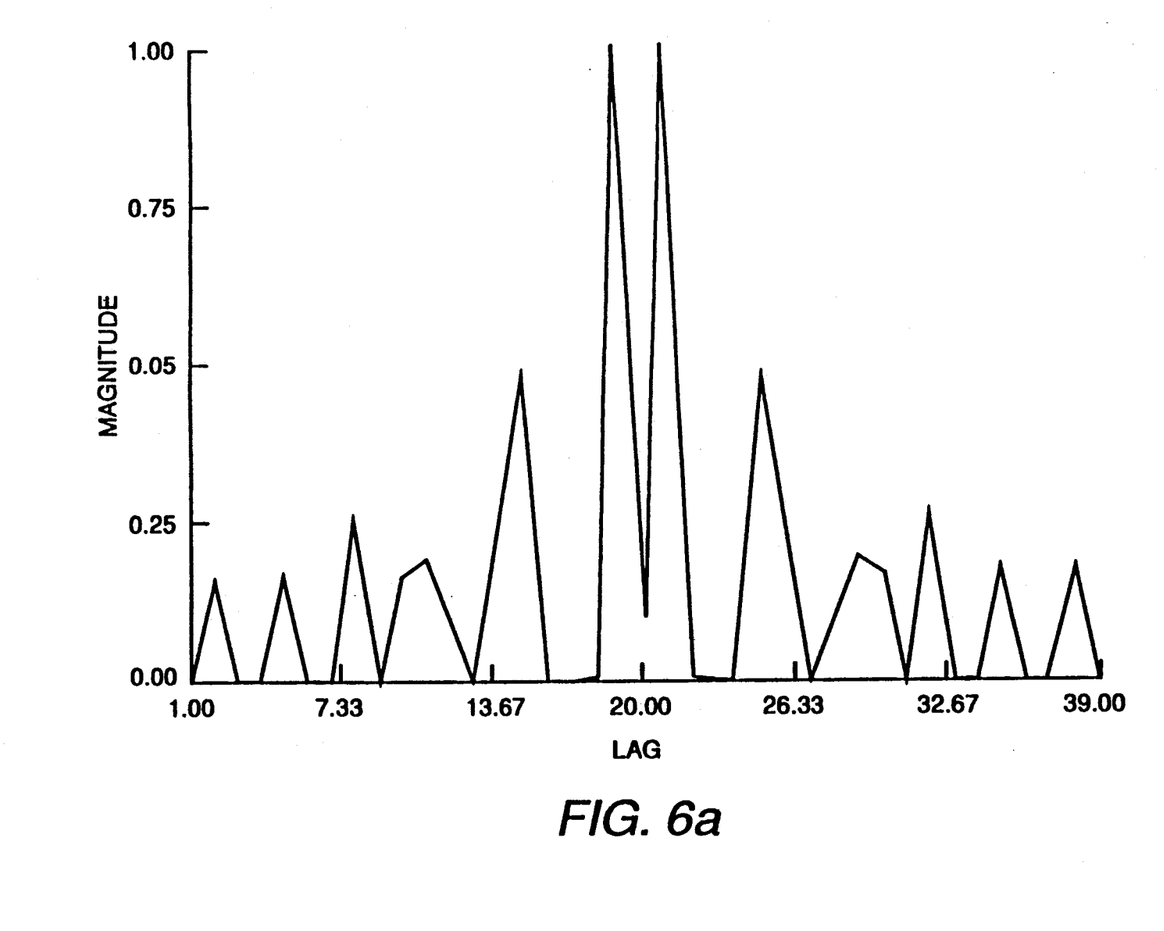
FIG. 6a and 6b illustrate computer simulation of magnitude and phase components of complex filtering coefficients as applied to the SAFT imaging system of FIG. 3.
Figure 6B:
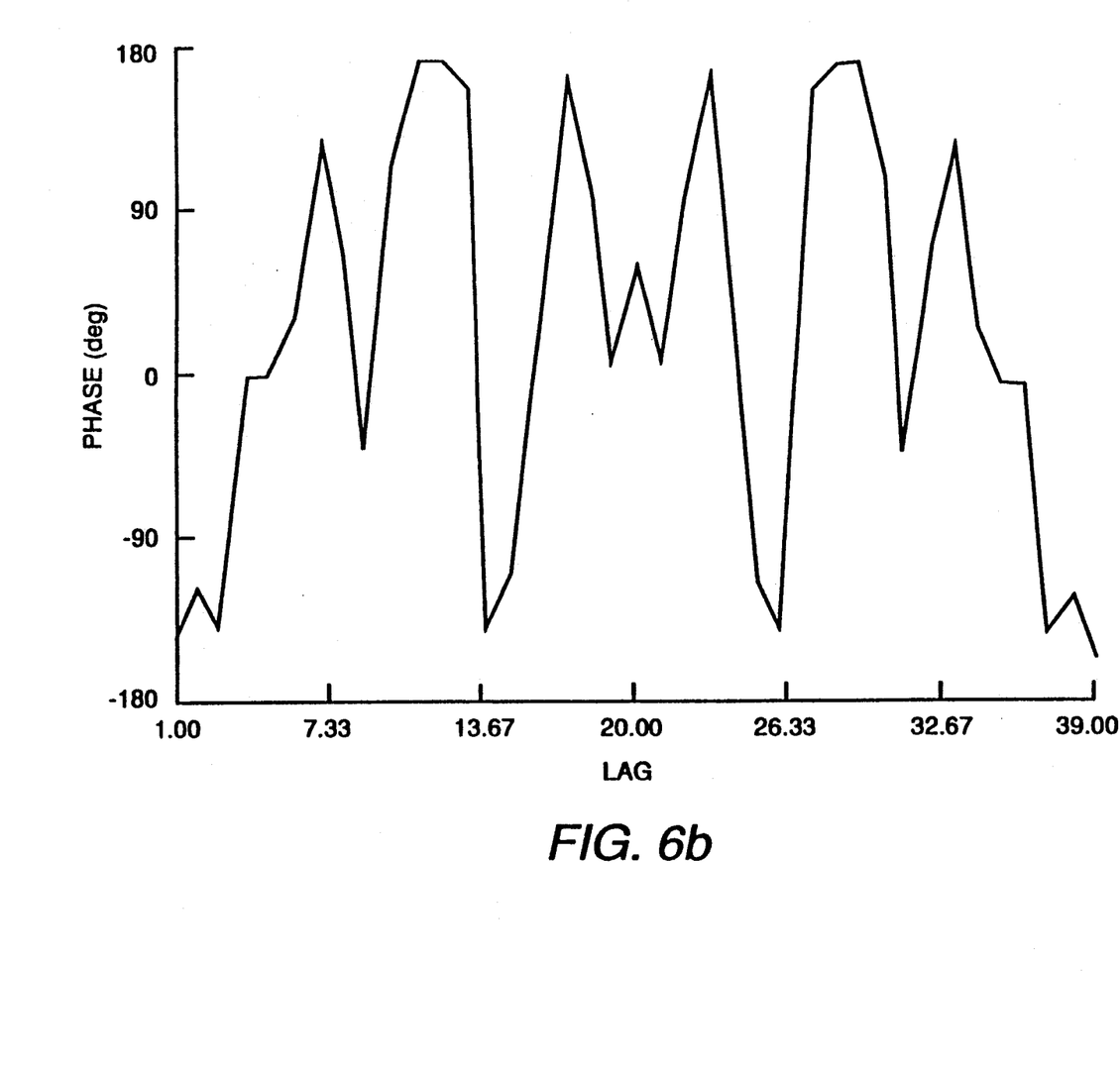
Figure 7:
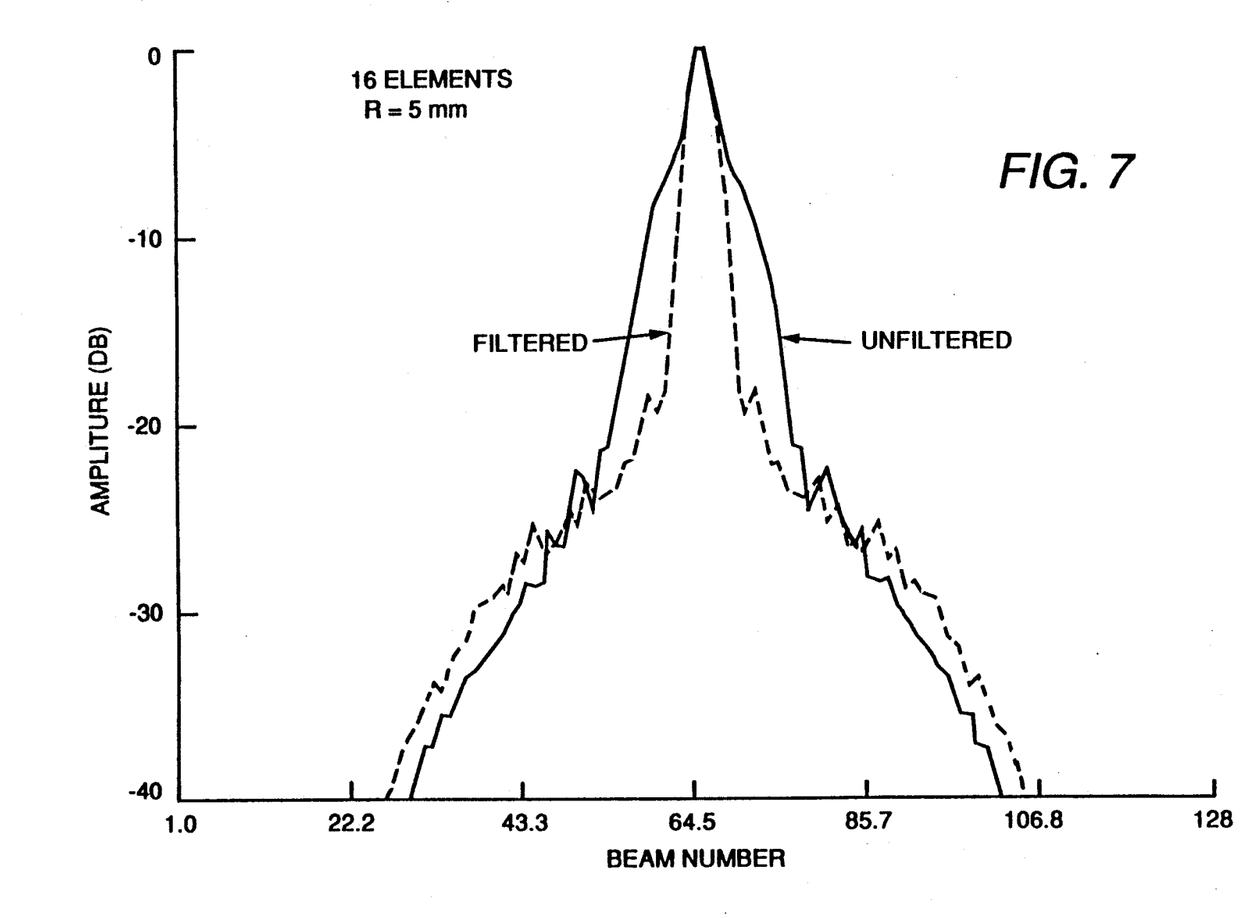
FIG. 7 illustrates a computer simulation comparing a resultant signal which has been complex filtered by the filter of FIGS. 6a and 6b to a correspondingly unfiltered resultant signal indicating improved beam formation in accordance with the invention.

To demonstrate the utility of this complex filter reconstruction based catheter system, a computer program for signal simulation was developed. In this computational simulation a 256 element, 50 MHz array was simulated on a 1.2 mm diameter circle. Each simulated firing simultaneously pulsed 16 channels (i.e. m=16) and 256 firings were recorded for each frame. A 39 point complex filter bank was generated for all ranges in accordance with commonly assigned copending patent application Ser. No. 07/767,460 as previously discussed. Computation of an array matrix comprising a bank of complex filter correction coefficients based on range and angle, θ, is illustrated in FIG. 5. The complex filter coefficients, expressed as signal magnitude and phase, for a target at a range of 5 mm from the origin of the circle are computationally simulated and presented as FIGS. 6a and 6b respectively. These resultant signal components represent complex filtering in angle, θ, only; to accommodate focusing at all ranges. Both components are presented as a function of the 'lag' time which represents scanning time for the complex filter. A collective beam pattern resulting from this filtered signal is then compared to a similar but unfiltered signal in FIG. 7 to gauge the improvement in beam formation provided by complex filtering. Complex filtering as shown in FIG. 7 results in an improvement of 3 dB resolution of 350 μm and an improvement of 20 dB resolution of about 1 mm at a 5 mm range. This is equivalent to a perfect lens focused at this range with an f/number of about 10-12 (i.e. an equivalent aperture of about 0.4-0.5 mm or 13-17 λ). The hardware needed to perform complex filtering is very inexpensive since only a 39 point wide line buffer and a 39 point deep complex filter bank (see FIG. 5) are needed to serve the entire reconstruction process. Although both conceptually and practically very simple to implement, the reconstruction system herein described assumes that the object being focused remains stationary over the number of beams needed to prime the complex filter bank. This is not difficult to ensure as the pulse repetition interval for a system such as this will be on the order of 20 μsec. All the signals needed for a particular beam to be properly filtered can be obtained within 700-800 μsec. Occasional motion artifacts that may occur can be minimized by employing simple averaging or more refined filtering using frame-to-frame processing. Filtering of this type will not temporally diffuse the appearance of the final image as acoustic frame intervals are of the order of 5 msec, a time much shorter in duration than the interval duration of any relevant motion occurring within the blood vessel.

While specific embodiments of the invention have been illustrated and described herein, it is realized that numerous modifications and changes will occur to those skilled in the art. It is therefore understood that the appended claims are intended to cover all modifications and changes as fall within the true spirit and scope of the invention.

What is claimed is:

1. A method of acquiring a plurality of pulse/echo signals obtained from a corresponding plurality of ultrasound transducer elements for imaging thereof comprising:

disposing said elements in an array around a catheter for intravascular placement;

providing a pulse capable of exciting said elements;

sequentially sampling said plurality of elements in order to fully multiplex an incrementally stepped contiguous subset thereof operating as a transceiver subarray on each consecutive excitation pulse;

fully multiplexing signals transmitted and received from each sequential transceiver subarray in a parallel manner on each consecutive excitation pulse;

maintaining a consecutively equivalent subarray by incrementally sampling array elements on each excitation pulse; and dynamically focusing said multiplexed signals by characterizing said transceiver subarray as a subset of a synthetic aperture array; wherein respective echo signals derived from each excitation pulse are retrospectively time delayed, demodulated into respective complex components, respectively component weighted by complex filtering according to range and summed over said synthetic aperture array.

2. Method according to claim 1 wherein said step of disposing further comprises providing sufficient number and spacing of array elements to accommodate adequate beam directivity.

3. Method according to claim 1 wherein said step of disposing further comprises providing sufficient number and spacing of array elements to accommodate the Nyquist criterion upon sampling thereof.

4. Method according to claim 1 wherein said step of providing said excitation pulse further includes providing at least a 50 MHz pulse.

5. Method according to claim 1 wherein said step of disposing said array further includes circumferentially disposing said array about a cylindrical catheter, cross-sectionally comprising a circular array.

6. Method according to claim 5 wherein said step of sequentially sampling further includes selecting a subaperture by sequentially decrementing one element of the circumferentially disposed array from said multiplexor and incrementing the next sequential element to said multiplexor in order to incrementally sample throughout said circular array.

7. Method of claim 5 wherein said step of circumferentially disposing further includes disposing a sufficiently large subset of elements to provide matched signal impedance.

8. Apparatus for catheter based ultrasound imaging of coronary vessels comprising:
   a plurality of ultrasound transducers disposed about a catheter;
   a multiplexor disposed in said catheter being controlled by a single cable in order to make parallel connection to a subset of said array elements operating as a transceiver subarray of a synthetic aperture transducer array on each excitation pulse;
   a controller disposed external to said catheter being coupled to said multiplexor in order to electronically control sampling of said transducer array to selectively connect said subarray thereof for full signal multiplexing said multiplexor being coupled to a transmit/receive switch which amplifies signals on receive only;
   a summing circuit disposed within said catheter and coupled between said multiplexor and said transmit/receive switch; and
   imaging electronics disposed external to said catheter.

9. Apparatus according to claim 8 wherein said imaging electronics comprise:

analog circuits for transmitting an excitation pulse signal to said transmit/receive switch and receiving signals therefrom;
   digital baseband circuitry coupled to said analog circuits for detecting, digitizing and demodulating received analog signals into demodulated complex component digital signals;
   line buffer coupled to said digital baseband circuitry for storing at least one frame of demodulated component digital signals;
   complex filter coupled to said line buffer for dynamically providing complex filtering of demodulated component digital signals based on range; and
   real time display instrumentation for buffering and converting filtered digital component signals for real time display.

10. Apparatus according to claim 9 wherein said complex filter operates to retrospectively time delay respective signals from each individual subarray element of a total synthetic aperture, mathematically weighting each demodulated signal components accordingly then summing components over said plurality of elements comprising said synthetic aperture array.

11. Apparatus according to claim 9 wherein said plurality of ultrasound transducers is circumferrentially disposed about a cylindrical catheter whose outer diameter is no more than 1.2 mm.

12. Apparatus according to claim 11 wherein said catheter enclosed apparatus is housed within a 100 $\mu$m tubular annulus bounded by said outer diameter.

13. Apparatus according to claim 9 wherein at least one catheter interconnection in addition to power and ground is operationally required.

14. Apparatus according to claim 9 wherein said ultrasound transducers are piezoelectric elements disposed between a pair of electrodes.

* * * * *